(12) United States Patent
Yukumoto et al.

(10) Patent No.: US 8,946,307 B2
(45) Date of Patent: Feb. 3, 2015

(54) BIOMASS GASIFICATION GAS PURIFICATION SYSTEM AND METHOD AND METHANOL PRODUCTION SYSTEM AND METHOD

(75) Inventors: Atsuhiro Yukumoto, Minato-ku (JP); Wataru Matsubara, Minato-ku (JP); Shinya Tachibana, Minato-ku (JP); Toshiya Akiba, Minato-ku (JP); Katsuhiko Shinoda, Minato-ku (JP); Takeshi Amari, Minato-ku (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 0 days.

(21) Appl. No.: 13/702,810

(22) PCT Filed: Aug. 3, 2011

(86) PCT No.: PCT/JP2011/067798
§ 371 (c)(1),
(2), (4) Date: Dec. 7, 2012

(87) PCT Pub. No.: WO2012/020685
PCT Pub. Date: Feb. 16, 2012

(65) Prior Publication Data
US 2013/0085307 A1   Apr. 4, 2013

(30) Foreign Application Priority Data

Aug. 9, 2010 (JP) ................................. 2010-179080

(51) Int. Cl.
*B01D 53/48* (2006.01)
*C10K 1/02* (2006.01)
(Continued)

(52) U.S. Cl.
CPC . *B01D 53/48* (2013.01); *C10K 1/02* (2013.01); *C10K 1/004* (2013.01); *C10K 3/003* (2013.01);
(Continued)

(58) Field of Classification Search
CPC .... B01D 53/48; B01D 2258/05; B01D 45/00; C01B 3/38; C07C 29/152; C10K 1/02; C10K 1/004; C01K 3/003; C01K 3/006
USPC ................ 568/840; 518/702; 423/210; 95/90
See application file for complete search history.

(56) References Cited

U.S. PATENT DOCUMENTS 6,991,769 B2 * 1/2006 Kaneko et al. ................. 422/187
2007/0051043 A1 * 3/2007 Schingnitz et al. ............. 48/210
(Continued)

FOREIGN PATENT DOCUMENTS

EP   1 431 373    6/2004
JP   2001-240877  9/2001
(Continued)

OTHER PUBLICATIONS

WO2010/035430A1; Apr. 1, 2010; English translation.*
(Continued)

*Primary Examiner* — Jafar Parsa
*Assistant Examiner* — Medhanit Bahta
(74) *Attorney, Agent, or Firm* — Wenderoth, Lind & Ponack, L.L.P.

(57) ABSTRACT

A biomass gasification gas purification system includes a dust collector for removing dust in biomass gasification gas (containing tar components) acquired by gasifying biomass by a biomass gasification furnace, a desulfurizer for removing sulfur oxide components in the dust-removed biomass gasification gas, a pre-reforming reactor for reforming tar components in the desulfurized biomass gasification gas, a steam feed unit for feeding steam to an upstream side of the pre-reforming reactor, and a natural-gas feed unit for feeding natural gas on an upstream side of the desulfurizer.

3 Claims, 4 Drawing Sheets

(51) Int. Cl.
  *C07C 29/151* (2006.01)
  *C01B 3/38* (2006.01)
  *C07C 31/04* (2006.01)
  *C10K 1/00* (2006.01)
  *C10K 3/00* (2006.01)
  *C10K 1/32* (2006.01)
  *C10K 3/02* (2006.01)
  *C10L 5/44* (2006.01)
  *C07C 29/152* (2006.01)
  *B01D 45/00* (2006.01)

(52) U.S. Cl.
  CPC ............... *C07C 29/151* (2013.01); *C10K 1/024* (2013.01); *C10K 1/32* (2013.01); *C10K 3/006* (2013.01); *C10K 3/023* (2013.01); *C01B 3/38* (2013.01); *C10L 5/44* (2013.01); *C07C 29/152* (2013.01); *B01D 45/00* (2013.01); *C07C 31/04* (2013.01); *C10G 2300/1011* (2013.01); *C10G 2300/1025* (2013.01); *C10J 2300/0916* (2013.01); *C10J 2300/1665* (2013.01); *C01B 2203/0277* (2013.01); *C01B 2203/061* (2013.01); *C01B 2203/1258* (2013.01); *C01B 2203/1619* (2013.01); *C01B 2203/1623* (2013.01); *Y02E 50/18* (2013.01); *Y02E 50/32* (2013.01)
  USPC ............... 518/702; 568/840; 423/210; 95/90; 95/135

(56) References Cited

U.S. PATENT DOCUMENTS

2010/0249251 A1* 9/2010 Hilton .......................... 518/702
2011/0314736 A1* 12/2011 Crespin ......................... 48/202

FOREIGN PATENT DOCUMENTS

| JP | 2001-240878 | 9/2001 |
|----|----|----|
| JP | 2004-346285 | 12/2004 |
| JP | 2006-016470 | 1/2006 |
| JP | 2006-348155 | 12/2006 |
| JP | 2007-204558 | 8/2007 |
| JP | 2009-40862 | 2/2009 |
| JP | 2009-536262 | 10/2009 |
| JP | 2009-279473 | 12/2009 |
| JP | 2010-077219 | 4/2010 |
| JP | 2010-111779 | 5/2010 |
| JP | 2010111779 A * | 5/2010 |
| WO | 99/41329 | 8/1999 |
| WO | 03/018467 | 3/2003 |
| WO | 2007/131240 | 11/2007 |
| WO | WO 2010035430 A1 * | 4/2010 |

OTHER PUBLICATIONS

Tatsumi, K. et al. Patent No. JP2010111779A; May 20, 2010; English translation.*
Coll, R. et al. Fuel Processing Technology 2001, 74, 19-31.*
Written Opinion of the International Searching Authority issued Sep. 6, 2011 in International (PCT) Application No. PCT/JP2011/067798.
International Search Report issued Sep. 6, 2011 in International Application No. PCT/JP2011/067797.
Written Opinion of the International Searching Authority, with English translation, issued Sep. 6, 2011 in International Application No. PCT/JP2011/067797.
Extended Search Report issued Apr. 16, 2014, in corresponding European Application No. 11816351.8.
Heinz Hiller et al. "Gas Production, 5.4. Absorption Process", Dec. 15, 2006, Wiley-VCH Verlag GmbH & Co. KGaA, Weinheim, pp. 1, 90-118, and 162-163, XP002595382.
Carlo N. Hamelinck et al. "Future prospects for production of methanol and hydrogen from biomass" Journal of Power Sources, Jan. 2002, pp. 1-22.
Decision of a Patent Grant issued Apr. 1, 2014, in corresponding Janpanse Application No. 2010-179080 (with English translation).
Extended European Search Report issued Apr. 16, 2014, in corresponding European Application No. 11816350.0.
International Search Report issued Sep. 6, 2011 in International (PCT) Application No. PCT/JP2011/067798 with English translation.

* cited by examiner

BIOMASS GASIFICATION GAS PURIFICATION SYSTEM AND METHOD AND METHANOL PRODUCTION SYSTEM AND METHOD

FIELD

The present invention relates to a biomass gasification gas purification system, a biomass gasification gas purification method, a methanol production system, and a methanol production method.

BACKGROUND

The present invention relates to a biomass gasification gas purification system, a biomass gasification gas purification method, a methanol production system, and a methanol production system method that can efficiently use biomass as a feedstock and can acquire a clean gas feedstock usable for fuels or for producing liquid fuels such as alcohol.

Generally, biomass refers to organisms (for example, agricultural products or by-products, wood, or plants) that can be used as an energy source or an industrial material, and is generated by an action of solar energy, air, water, soil, and the like. Therefore, biomass can be reproduced unlimitedly.

Use of the biomass enables production of a clean energy source such as gas and methanol for fuels. Furthermore, biomass as waste can be treated, which contributes also to environmental cleanup, and biomass to be newly produced can be grown by photosynthesis while fixing $CO_2$. Because $CO_2$ in the air does not increase, the use of biomass leads to suppression of $CO_2$, and thus it is a favorable technique.

As biomass to be fed, it is preferable to feed produced or discarded biomass after being pulverized and dried. In the present invention, biomass refers to biological resources (for example, agricultural products or by-products, wood, or plants) that can be used as an energy source or an industrial material and, for example, plants such as sorghum, Napier grass, and Spirulina, and wood such as Japanese cedar, broad-leaved tree, and bark are used (Patent Literatures 1 and 2, and Non Patent Literature 1).

Meanwhile, gas produced by using the biomass as a feedstock contains fine particles, tar components, hydrogen sulfide, chlorine, and the like, and thus it is not suitable to use the gas as it is as gas for synthesizing a liquid fuel using a synthetic catalyst or an energy source for fuel cells. Accordingly, a method of removing minor components such as the fine particles, the tar components, the hydrogen sulfide, and the chlorine has been devised by using a separation device and a gas purification device. As a source gas for acquiring the liquid fuel and the energy source for fuel cells, for practical operation, the minor components need to be reduced to allowable content limits of tar, which is less than 1 mg/Nm³, and of sulfur content, which is less than 0.1 ppm. However, in the existing biomass gasification system, sufficient reduction of the minor components has not been realized yet.

Furthermore, the processing volume of the biomass gasification system is several hundred tons per day, which corresponds to a small-sized or medium-sized plant as compared to a typical gasification system using fossil fuels. In such a small-sized or medium-sized gasification system, it is preferable to include a simple and inexpensive gas purification line, which is an essential requirement in a so-called decentralized plant. Also in this regard, the existing biomass gasification system has not realized a simple and inexpensive gas purification line yet.

Conventionally, therefore, a biomass gasification system including a separation unit such as a cyclone that removes dust in produced gas gasified by a biomass gasification furnace, a cooler that cools dust-removed gas, and a gas purification device that purifies the cooled gas has been proposed (Patent Literature 3).

In the conventional gas purification device for biomass gasification gas, biomass is temporarily stored, and cooled produced gas having passed through the cooler is caused to pass through the gas purification device, where tar components contained in the cooled produced gas are adsorbed. Tar-adsorbed biomass from which the tar has been adsorbed is carried to a biomass feed unit by a carrier unit as purified gas.

There is another proposal of a fixed-bed removal device to which a remover layer for removing tar components is fixed (Patent Literature 4).

CITATION LIST

Patent Literatures

Patent Literature 1: Japanese Patent Application Laid-open No. 2001-240877
Patent Literature 2: Japanese Patent Application Laid-open No. 2001-240878
Patent Literature 3: Japanese Patent Application Laid-open No. 2004-346285
Patent Literature 4: Japanese Patent Application Laid-open No. 2006-016470

Non Patent Literature

Non Patent Literature 1: "Biomass fuel for the 21st Century", Masayasu SAKAI, Morikita Publishing Co., Ltd., published on 28 Oct. 1998

SUMMARY

Technical Problem

However, in the proposal described in Patent Literature 3, when of removing tar components with the gas purification device, the tar components cannot be removed or reduced to a level allowable for a synthetic catalyst.

Furthermore, in the proposal described in Patent Literature 4, treatment of activated carbon as a remover having adsorbed tar components is required separately.

As a method of removing (decomposing) tar (a hydrocarbon component having a high boiling point), a method of performing decomposition by a reforming reaction shown by the following formula (1) by using a pre-reforming catalyst (for example, Ni catalyst or Ru catalyst) can be considered. However, in biomass gasification gas, the concentration of CO components is quite high, and when a reaction is caused at a pressure of about 1 MPaG or less and at a temperature from 400° C. to 550° C., which is an optimum reaction temperature of the catalyst, there is a problem that a methanation reaction as shown in the following formulae (3) and (4) occurs as a side reaction.

The formula (2) is a combination of the formulae (3) and (4), which is referred to as a shift reaction.

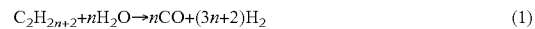
$$C_2H_{2n+2} + nH_2O \rightarrow nCO + (3n+2)H_2 \tag{1}$$

$$CO + H_2O \rightarrow CO_2 + H_2 \tag{2}$$

$$CO + 3H_2 \rightarrow CH_4 + H_2O \tag{3}$$

$$CO_2 + 4H_2 \rightarrow CH_4 + 2H_2O \tag{4}$$

As the pre-reforming catalyst, for example, "ReforMax 100" (trade name) and "ReforMax 100RS, N. E" (trade name) manufactured by Sud-Chemie AG, "E Catalyst" (trade name) and "NI-3266E" (trade name) manufactured by N. E. Chemcat Corporation, and "RKNGR, AR-401" (trade name) manufactured by Haldor Topsøe A/S are commercially available.

The methanation reaction shown by the formulae (3) and (4) is an exothermic reaction. Therefore, when a pre-reforming reactor including an insulated pre-reforming catalyst is used, the reaction occurs at a temperature of 550° C. higher than an appropriate temperature for the pre-reforming catalyst. Accordingly, sintering or coking occurs and also thermal runaway may occur, which prevents satisfactory gas purification from being stably performed.

The present invention has been achieved to solve the above problems, and an object of the present invention is to provide a biomass gasification gas purification system, a biomass gasification gas purification method, a methanol production system, and a methanol production method in which tar components in gas produced by biomass gasification are efficiently reformed, and thermal runaway does not occur.

Solution to Problem

According to a first aspect of the present invention in order to solve the above problems, there is provided a biomass gasification gas purification system including: a dust collector that collects dust to remove it from biomass gasification gas acquired by gasifying biomass by a biomass gasification furnace; a desulfurizer that removes sulfur oxide components in dust-removed biomass gasification gas; a pre-reforming reactor that reforms tar components in desulfurized biomass gasification gas; and a natural-gas feed unit that feeds natural gas on an upstream side of the desulfurizer or the pre-reforming reactor.

According to a second aspect of the present invention, there is provided a biomass gasification gas purification system including: a dust collector that collects dust to remove it from biomass gasification gas acquired by gasifying biomass by a biomass gasification furnace; a desulfurizer that removes sulfur oxide components in dust-removed biomass gasification gas; and a pre-reforming reactor that reforms tar components in desulfurized biomass gasification gas; and a steam feed unit that feeds steam to an upstream side of the pre-reforming reactor.

According to a third aspect of the present invention, there is provided a biomass gasification gas purification system including: a dust collector that collects dust to remove it from biomass gasification gas acquired by gasifying biomass by a biomass gasification furnace; a desulfurizer that removes sulfur oxide components in dust-removed biomass gasification gas; a pre-reforming reactor that reforms tar components in desulfurized biomass gasification gas; and a steam feed unit that feeds steam to an upstream side of the pre-reforming reactor; and a natural-gas feed unit that feeds natural gas on an upstream side of the desulfurizer or the pre-reforming reactor.

According to a fourth aspect of the present invention, there is provided a methanol production system including: the biomass gasification gas purification system according to any one of the first to third aspects; a boosting device that boosts pre-reformed biomass gasification gas; and a methanol synthesis apparatus that synthesizes methanol by using boosted gas.

According to a fifth aspect of the present invention, there is provided the methanol production system according to the fourth aspect, including a reforming reactor that reforms the boosted gas.

According to a sixth aspect of the present invention, there is provided a biomass gasification gas purification method including: collecting dust to remove it from biomass gasification gas acquired by gasifying biomass by a biomass gasification furnace; desulfurizing sulfur oxide components in dust-removed biomass gasification gas; and feeding natural gas to a pre-reforming reactor at a time of reforming tar components in desulfurized biomass gasification gas by the pre-reforming reactor.

According to a seventh aspect of the present invention, there is provided a biomass gasification gas purification method including: collecting dust to remove it frombiomass gasification gas acquired by gasifying biomass by a biomass gasification furnace; desulfurizing sulfur oxide components in dust-removed biomass gasification gas; and reforming tar components in desulfurized biomass gasification gas by a pre-reforming reactor while feeding steam.

According to an eighth aspect of the present invention, there is provided a biomass gasification gas purification method including: collecting dust to remove it from biomass gasification gas acquired by gasifying biomass by a biomass gasification furnace; desulfurizing sulfur oxide components in dust-removed biomass gasification gas; and feeding natural gas to a pre-reforming reactor at a time of reforming tar components in desulfurized biomass gasification gas by the pre-reforming reactor while feeding steam.

According to a ninth aspect of the present invention, there is provided a methanol production method including: purifying biomass gasification gas by the biomass gasification gas purification method according to any one of the sixth to eighth aspects; boosting pre-reformed biomass gasification gas; and synthesizing methanol by using boosted gas.

According to a tenth aspect of the present invention, there is provided the methanol production method according to the ninth aspect, including reforming the boosted gas.

Advantageous Effects of Invention

According to the present invention, the methanation reaction as a side reaction is suppressed and thermal runaway of the reforming reactor is suppressed by introducing at least one of natural gas and steam or both thereof at the time of reforming tar components in the biomass gasification gas having a high concentration of CO components, thereby enabling stabilized gas purification of biomass gasification gas.

DESCRIPTION OF EMBODIMENTS

The present invention will be explained below in detail with reference to the accompanying drawings. The present invention is not limited to the following embodiments. In addition, constituent elements in the following embodiments include those that can be easily anticipated by persons skilled in the art or that are substantially equivalent.

First Embodiment

Figure 1:
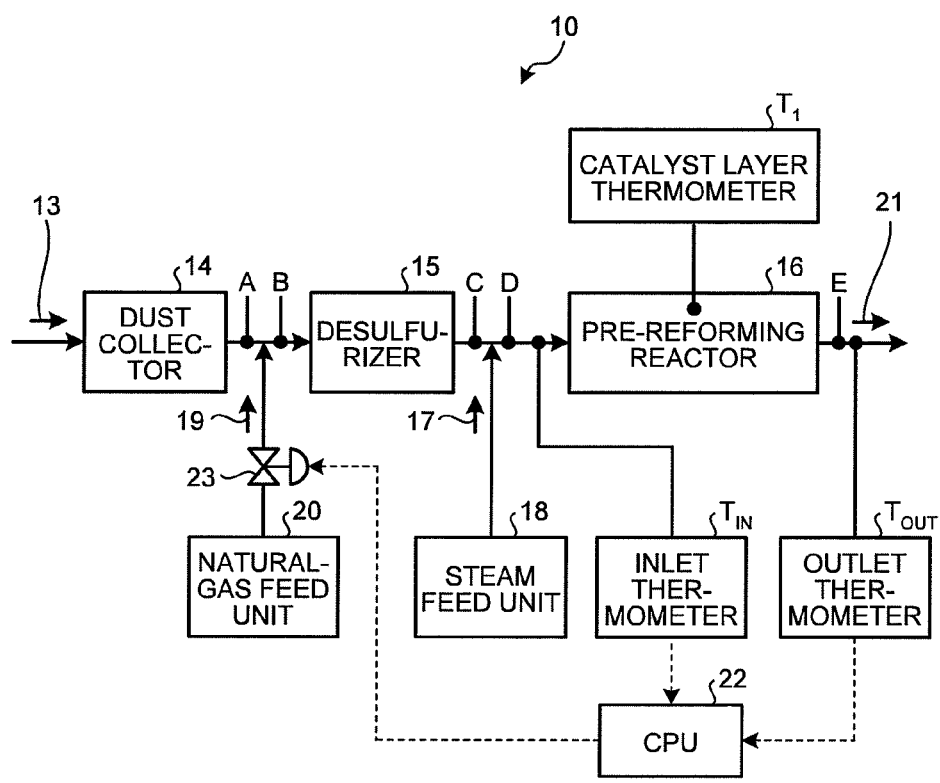
FIG. 1 is a schematic diagram of a biomass gasification gas purification system.

A biomass gasification gas purification system according to a first embodiment of the present invention is explained with reference to the drawings. FIG. 1 is a schematic diagram of the biomass gasification gas purification system.

As shown in FIG. 1, a biomass gasification gas purification system 10 includes a dust collector (cyclone, scrubber, or the like) 14 that collects dust to remove it from biomass gasification gas (containing tar components) 13 acquired by gasifying biomass by a biomass gasification furnace, a desulfurizer 15 that removes sulfur oxide components in the dust-removed biomass gasification gas 13, a pre-reforming reactor 16 that reforms the tar components in the desulfurized biomass gasification gas 13, a steam feed unit 18 that feeds steam 17 to an upstream side of the pre-reforming reactor 16, and a natural-gas feed unit 20 that feeds natural gas (main component: methane) 19 on an upstream side of the desulfurizer 15. In FIG. 1, reference numeral 21 denotes synthesis gas, 22 denotes a controller (CPU), 23 denotes an adjustment valve that adjusts an introduced amount of the natural gas, reference character $T_{IN}$ denotes an inlet thermometer that measures a temperature on an inlet side of the pre-reforming reactor 16, $T_{OUT}$ denotes an outlet thermometer that measures a temperature on an outlet side of the pre-reforming reactor 16, $T_1$ denotes a catalyst layer thermometer that measures a temperature of a catalyst layer, and A to E denote measurement positions.

Because progress of the methanation reaction is caused by a large amount of CO components in the biomass gasification gas 13, methanation can be suppressed by calculating an equilibrium composition in each temperature range in the following formula (3). Therefore, either the steam or the natural gas (main component: methane) is introduced to achieve suppression of methanation.

$$CO + 3H_2 \rightarrow CH_4 + H_2O \quad (3)$$

The introduced amount of natural gas (main component: methane) can be calculated from an equilibrium constant to keep the temperature at equal to or lower than 550° C., which is an upper temperature limit of the catalyst of the pre-reforming reactor 16.

Results obtained by measuring the concentration of components at the respective measurement positions (A to E) when the natural gas 19 is introduced on the upstream side of the desulfurizer 15 as in the present invention are shown in Table 1.

As shown in Table 1, under the condition of S/C=3, which is a ratio between steam ($H_2O$) in source gas and an amount of carbon in carbon hydride in the source gas, a feed rate of steam (44.5 kgmol/h) and a feed rate of natural gas (main component: methane) (11.3 kgmol/h) are obtained from the respective components, and then the steam 17 is fed by the steam feed unit 18 and the natural gas 19 is fed by the natural-gas feed unit 20.

In Table 1, C2+ denotes a total of hydrocarbon components such as ethane, propane, and butane contained in natural gas.

As the respective measurement positions in Table 1, the position A is at an outlet of the dust collector 14 and before feed of the natural gas 19. The position B is at an outlet of the dust collector 14 and after the feed of the natural gas 19. The position C is at an outlet of the desulfurizer 15 and before feed of the steam 17. The position D is at an outlet of the desulfurizer 15 and after the feed of the steam 17. The position E is at an outlet of the pre-reforming reactor 16.

TABLE 1

| | | | | | | | | | | |
|---|---|---|---|---|---|---|---|---|---|---|
| <S/C = 3, with introduction of natural gas> | | | | | | | | | | |
| | | POS. | | | | | | | | |
| | A | | B | | C | | D | | E | |
| Phase | Vapor | | Vapor | | Vapor | | Vapor | | Vapor | |
| Temp(° C.) | 40 | | 300 | | 300 | | 400 | | 550 | |
| Pressure (kg/cm²G) | 0.3 | | 4.8 | | 4.4 | | 4.2 | | 4.0 | |
| Mole Weight | 23.19 | | 22.23 | | 22.23 | | 20.54 | | 21.10 | |
| COMP. | kgmol/h | MOL % | kgmol/h | MOL % | kgmol/h | MOL % | kgmol/h | MOL % | kgmol/h | MOL % |
| CO | 11.5 | 21.1 | 11.5 | 17.4 | 11.5 | 17.4 | 11.5 | 10.4 | 3.4 | 3.1 |
| CO₂ | 16.8 | 30.9 | 17.2 | 26.0 | 17.2 | 26.0 | 17.2 | 15.6 | 24.3 | 22.6 |
| METHANE | 2.4 | 4.3 | 13.7 | 20.7 | 13.7 | 20.7 | 13.7 | 12.4 | 17.4 | 16.1 |
| H₂ | 18.6 | 34.1 | 18.6 | 28.1 | 18.6 | 28.1 | 18.6 | 16.8 | 20.0 | 18.6 |
| H₂O | 2.7 | 4.9 | 2.0 | 3.1 | 2.0 | 3.1 | 46.5 | 42.0 | 40.5 | 37.6 |
| C2+ | 0.0 | 0.0 | 0.6 | 0.9 | 0.6 | 0.9 | 0.6 | 0.5 | 0.0 | 0.0 |
| | kgmol/h | ppm | kgmol/h | ppm | kgmol/h | ppm | kgmol/h | ppm | kgmol/h | ppm |
| Tar components | 0.3 | 6968.6 | 0.3 | 5744.1 | 0.3 | 5744.3 | 0.3 | 3434.4 | 0.0 | 0.0 |

On the other hand, as shown in Table 2, when natural gas (methane) is not fed under the condition of S/C=3, methanation cannot be suppressed, and the temperature rises up to 640° C. largely exceeding the upper temperature limit (for example, 550° C.) of the catalyst of the pre-reforming reactor 16, resulting in a temperature higher than an allowable catalyst temperature.

TABLE 2

<S/C = 3, without introduction of natural gas>

| | POS. | | | | | | | | | |
|---|---|---|---|---|---|---|---|---|---|---|
| | A | | B | | C | | D | | E | |
| Phase | Vapor | | Vapor | | Vapor | | Vapor | | Vapor | |
| Temp(° C.) | 40 | | 300 | | 300 | | 400 | | 640 | |
| Pressure (kg/cm²G) | 0.3 | | 4.8 | | 4.4 | | 4.2 | | 4.0 | |
| Mole Weight | 23.19 | | 23.25 | | 23.25 | | 22.68 | | 24.54 | |
| COMP. | kgmol/h | MOL % | kgmol/h | MOL % | kgmol/h | MOL % | kgmol/h | MOL % | kgmol/h | MOL % |
| CO | 11.5 | 21.1 | 11.5 | 21.4 | 11.5 | 21.4 | 11.5 | 19.1 | 9.3 | 16.6 |
| CO₂ | 16.8 | 30.9 | 16.8 | 31.3 | 16.8 | 31.3 | 16.8 | 27.9 | 17.2 | 30.8 |
| METHANE | 2.4 | 4.3 | 2.4 | 4.4 | 2.4 | 4.4 | 2.4 | 3.9 | 5.5 | 9.9 |
| H₂ | 18.6 | 34.1 | 18.6 | 34.6 | 18.6 | 34.6 | 18.6 | 30.8 | 11.6 | 20.8 |
| H₂O | 2.7 | 4.9 | 2.0 | 3.8 | 2.0 | 3.8 | 8.6 | 14.2 | 10.1 | 18.1 |
| C2+ | 0.0 | 0.0 | 0.0 | 0.0 | 0.0 | 0.0 | 0.0 | 0.0 | 0.0 | 0.0 |
| | kgmol/h | ppm | kgmol/h | ppm | kgmol/h | ppm | kgmol/h | ppm | kgmol/h | ppm |
| Tar components | 0.3 | 6969.1 | 0.3 | 7055.8 | 0.3 | 7057.5 | 0.3 | 6292.3 | 0.0 | 0.0 |

As shown in Table 3, when only steam is fed, thermal runaway due to methanation can be suppressed by introducing steam excessively (74.9 kgmol/h) and setting S/C to "27".

In this case, however, while the gas reforming proceeds further than that in a conventional case, the feed rate of steam increases and thus the system efficiency decreases, which is not desirable.

Figure 2:
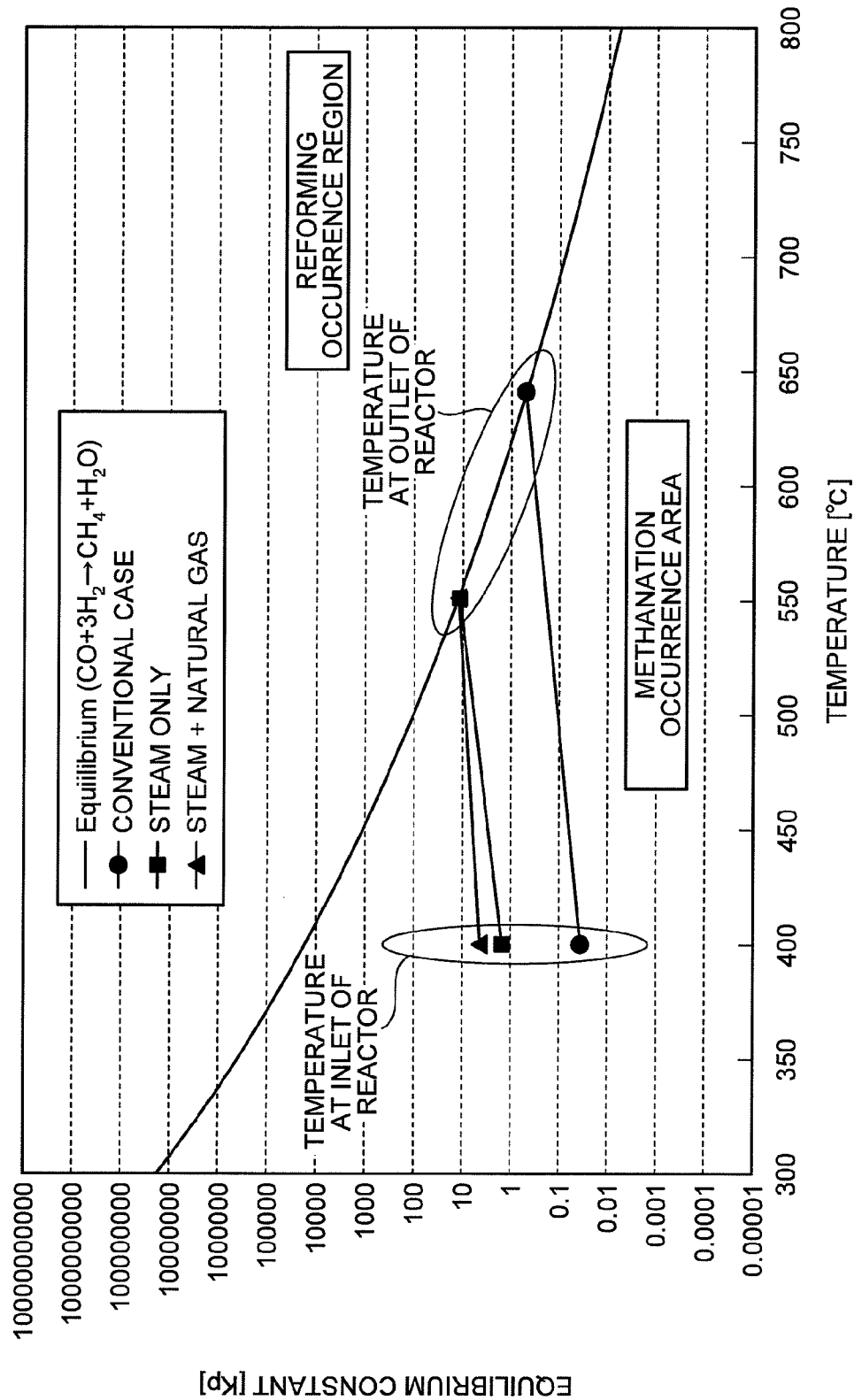
FIG. 2 is a relationship diagram between a reaction temperature and an equilibrium constant in a methanation occurrence region and a reforming occurrence region of CO.

The equilibrium constant (Kp) corresponding to a relational expression of FIG. 2 is shown by the following formula (5).

$$\text{Equilibrium constant}(Kp) = ([CH_4] \times [H_2O])/([CO] \times [H_2]^3) \quad (5)$$

where [ ] denotes a partial pressure of gas components.

TABLE 3

<S/C = 27, with excessive steam>

| | POS. | | | | | | | | | |
|---|---|---|---|---|---|---|---|---|---|---|
| | A | | B | | C | | D | | E | |
| Phase | Vapor | | Vapor | | Vapor | | Vapor | | Vapor | |
| Temp(° C.) | 40 | | 300 | | 300 | | 400 | | 550 | |
| Pressure (kg/cm²G) | 0.3 | | 4.8 | | 4.4 | | 4.2 | | 4.0 | |
| Mole Weight | 23.19 | | 23.25 | | 23.25 | | 20.21 | | 20.79 | |
| COMP. | kgmol/h | MOL % | kgmol/h | MOL % | kgmol/h | MOL % | kgmol/h | MOL % | kgmol/h | MOL % |
| CO | 11.5 | 21.1 | 11.5 | 21.4 | 11.5 | 21.4 | 11.5 | 9.0 | 2.1 | 1.6 |
| CO₂ | 16.8 | 30.9 | 16.8 | 31.3 | 16.8 | 31.3 | 16.8 | 13.1 | 24.9 | 19.9 |
| METHANE | 2.4 | 4.3 | 2.4 | 4.4 | 2.4 | 4.4 | 2.4 | 1.8 | 5.1 | 4.1 |
| H₂ | 18.6 | 34.1 | 18.6 | 34.6 | 18.6 | 34.6 | 18.6 | 14.5 | 20.7 | 16.6 |
| H₂O | 2.7 | 4.9 | 2.0 | 3.8 | 2.0 | 3.8 | 76.9 | 59.7 | 70.2 | 56.2 |
| C2+ | 0.0 | 0.0 | 0.0 | 0.0 | 0.0 | 0.0 | 0.0 | 0.0 | 0.0 | 0.0 |
| | kgmol/h | ppm | kgmol/h | ppm | kgmol/h | ppm | kgmol/h | ppm | kgmol/h | ppm |
| Tar components | 0.3 | 6970.1 | 0.3 | 7062.1 | 0.3 | 7056.9 | 0.3 | 1027.8 | 0.0 | 0.0 |

FIG. 2 is a relationship diagram between a reaction temperature and an equilibrium constant in a methanation occurrence region and a reforming occurrence region of CO. In FIG. 2, a region below an equilibrium constant curve is the methanation occurrence region, and a region above the equilibrium constant curve is the reforming occurrence region.

In FIG. 2, a black triangular plot corresponds to Table 1, black circular plots correspond to Table 2, and black square plots correspond to Table 3.

An equilibrium constant value (Kp=12) corresponding to the allowable catalyst temperature (for example, 550° C.) is obtained from FIG. 2, and a feedstock composition at the inlet of the reactor required for achieving the equilibrium constant value at the outlet of the reactor can be obtained based on the formula (5) and reaction calculation and calculation of a heat generation amount and a heat absorption amount of formulae (1) to (4). The introduced amounts of natural gas (main component: methane) and steam are determined to realize the feedstock composition.

Even if natural gas (methane) is fed beforehand, occurrence of methanation changes in some reaction conditions. Therefore, the allowable temperature (Tmax: 550° C.) of the pre-reforming reactor 16 is monitored by the outlet thermometer $T_{OUT}$ and the catalyst layer thermometer $T_1$, and when the temperature approaches the allowable temperature (Tmax: 550° C.), the controller (CPU) 22 executes a control to adjust the adjustment valve 23 to increase natural gas (main component: methane), thereby increasing the introduced amount of the natural gas 19.

In this way, the concentration of natural gas (main component: methane) in the gas is increased by feeding natural gas (main component: methane) on the upstream side of the pre-reforming reactor 16, thereby suppressing the methanation reaction and an increase in temperature. Accordingly, the temperature does not rise to the upper temperature limit of the catalyst of the pre-reforming reactor 16 or higher, deterioration (sintering or the like) of the catalyst does not occur, and satisfactory tar reforming can be performed.

In the present embodiment, the natural gas 19 is introduced on the upstream side of the desulfurizer 15. However, when the natural gas 19 contains fewer S (sulfur) components, the natural gas 19 can be introduced from the same position as that of the steam 17 on the upstream side of the pre-reforming reactor 16 because there is no poisoning of the catalyst.

Furthermore, there may be a surplus of steam in some biomass gasification plants. In this case, only steam can be introduced. When natural gas can be acquired at a low cost, only natural gas can be introduced without introducing steam.

The acquired synthesis gas 21 can be directly used as fuel gas for a gas turbine. By adjusting compositions of $H_2$ and CO gas in the synthesis gas, the synthesis gas 21 can be used also as gas for producing chemical products such as ammonia and methanol (or dimethyl ether). A system using the acquired gas for methanol synthesis is explained below.

Second Embodiment

Figure 3:
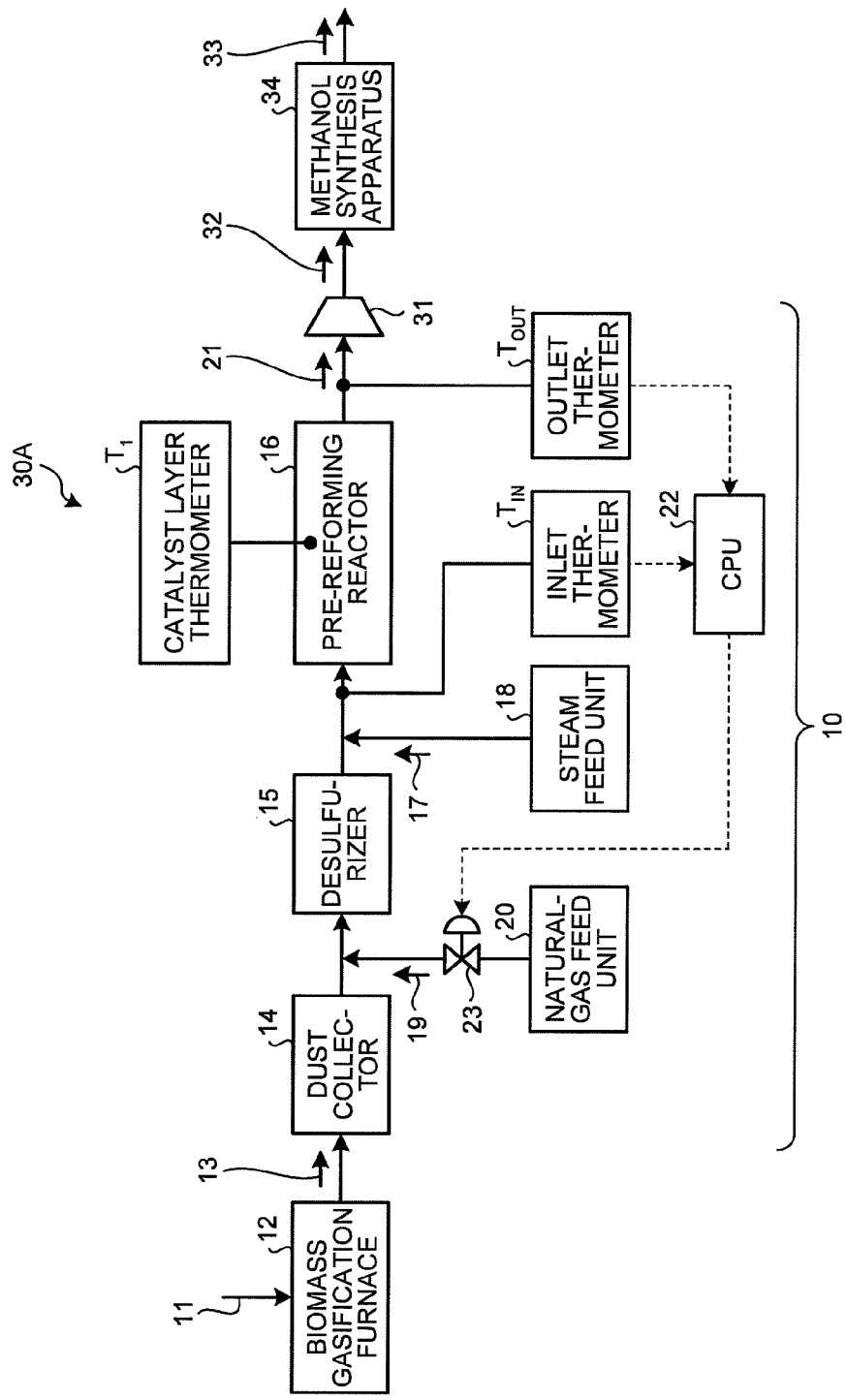
FIG. 3 is a schematic diagram of a methanol production system according to a second embodiment of the present invention.
Figure 4:
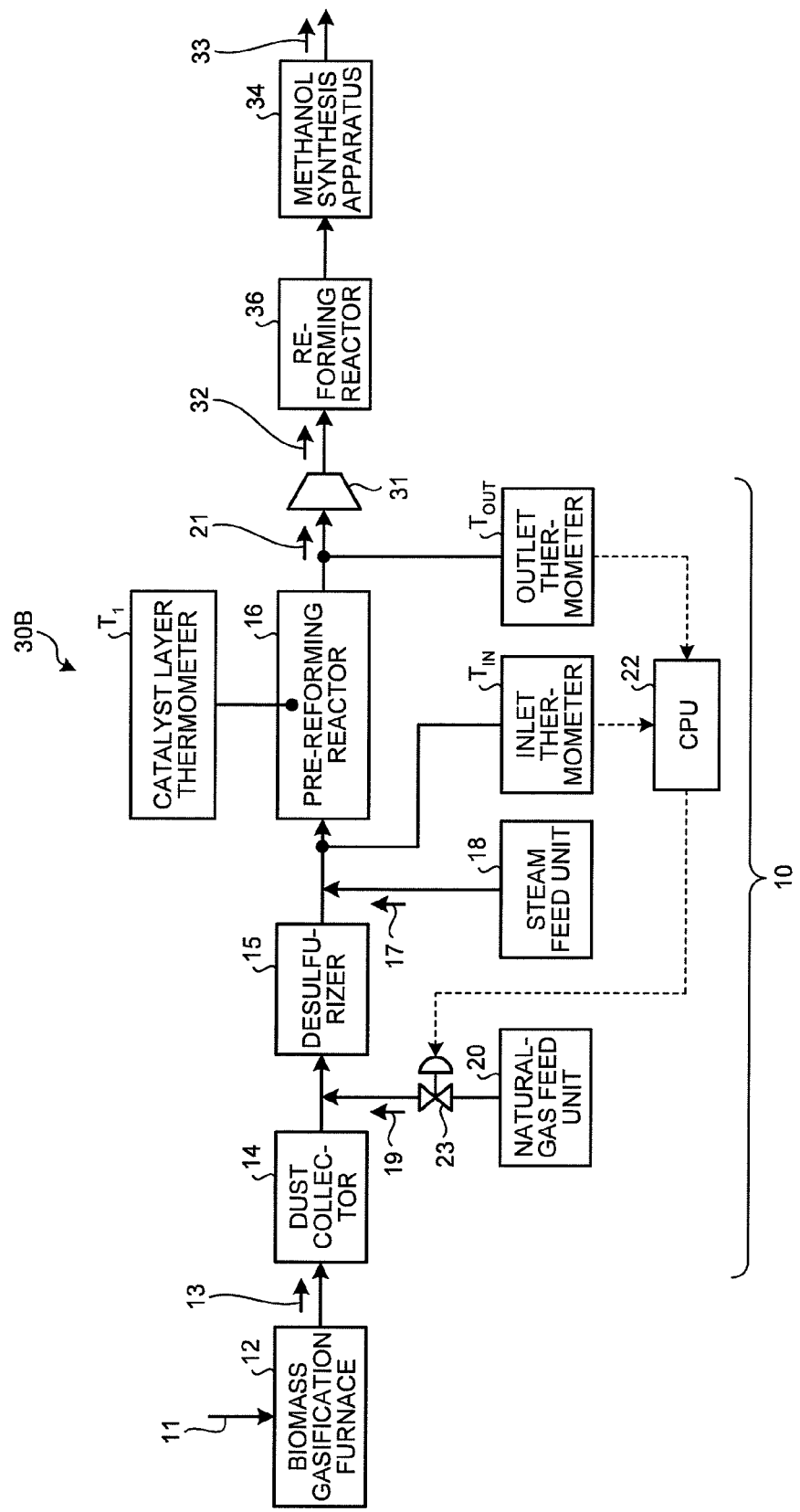
FIG. 4 is a schematic diagram of another methanol production system according to the second embodiment.

A methanol production system according to a second embodiment of the present invention is explained with reference to the drawings. FIG. 3 is a schematic diagram of the methanol production system according to the second embodiment. FIG. 4 is a schematic diagram of another methanol production system according to the second embodiment.

As shown in FIG. 3, a methanol production system 30A includes a biomass gasification furnace 12 that gasifies biomass 11, the dust collector 14 that collects dust to remove it from the biomass gasification gas (containing tar components) 13 acquired by gasification, the desulfurizer 15 that removes sulfur oxide components in the dust-removed biomass gasification gas 13, the pre-reforming reactor 16 that reforms the tar components in the desulfurized biomass gasification gas 13, the steam feed unit 18 that feeds the steam 17 to the upstream side of the pre-reforming reactor 16, the natural-gas feed unit 20 that feeds the natural gas 19 on the upstream side of the desulfurizer 15, a boosting device 31 that boosts the synthesis gas 21 of the pre-reformed biomass gasification gas, and a methanol synthesis apparatus 34 that synthesizes methanol 33 by using boosted gas 32.

The biomass gasification gas purification system 10 according to the first embodiment shown in FIG. 1 corresponds to components from the dust collector 14 to the pre-reforming reactor 16.

According to the present embodiment, when the tar components in the biomass gasification gas 13 are reformed in the biomass gasification gas purification system 10, the natural gas 19 can be introduced to stably perform reforming of tar components. Accordingly, stable methanol synthesis can be performed for gas from which the tar components have been removed, without deteriorating the methanol synthesis catalyst.

In the present invention, it is preferable to feed produced or discarded biomass after being pulverized and dried as the biomass 11 to be fed into the biomass gasification furnace 12. Biomass in the present invention refers to biological resources (for example, agricultural products or by-products, wood, or plants) that can be used as an energy source or an industrial material, and plants such as sorghum, Napier grass, and Spirulina, and wood such as Japanese cedar, broad-leaved tree, and bark can be cited as examples. In the present invention, it is preferable that an average grain diameter (D) of the pulverized biomass 11 is 0.05 mm≤D≤5 mm. This is because when the average grain diameter is smaller than 0.05 millimeter, the pulverization efficiency of biomass decreases, which is not desirable. On the other hand, when the average grain diameter exceeds 5 millimeters, satisfactory burning does not proceed up to the inside of biomass, any reaction is not accelerated, and highly efficient gasification becomes difficult. In the present invention, a combustion oxidizer to be fed to the biomass gasification furnace is preferably a mixture of air and steam or oxygen and steam.

Furthermore, because the natural gas (main component: methane) 19 is introduced in the biomass gasification gas purification system 10, a reforming reactor 36 that reforms the boosted gas 32 is provided in a methanol production system 30B according to a modification of the second embodiment as shown in FIG. 4 to perform gas reforming and decrease the concentration of methane, which does not contribute to methanol synthesis, thereby improving methanol synthesis yields.

REFERENCE SIGNS LIST 10 biomass gasification gas purification system
11 biomass
12 biomass gasification furnace
13 biomass gasification gas (containing tar components)
14 dust collector
15 desulfurizer
16 pre-reforming reactor
17 steam
19 natural gas

The invention claimed is:

1. A biomass gasification gas purification method comprising:
  gasifying biomass so as to produce biomass gasification gas;
  removing dust in the biomass gasification gas;
  desulfurizing sulfur oxide components in the biomass gasification gas that has had the dust removed therefrom so as to produce desulfurized biomass gasification gas;
  reforming tar components in the desulfurized biomass gasification gas using a pre-reforming reactor, the pre-reforming reactor having a catalyst with an allowable catalyst temperature;
  feeding at least one of natural gas and steam to the pre-reforming reactor during said reforming of tar components;
  obtaining an equilibrium constant from partial pressures of $CH_4$, $H_2O$, CO and $H_2$ at an outlet of the pre-reforming reactor; and
  determining amounts of the natural gas and steam feeding to the pre-reforming reactor in said feeding at least one of natural gas and steam to the pre-reforming reactor so that the equilibrium constant that is obtained from the partial pressures of $CH_4$, $H_2O$, CO and $H_2$ at the outlet of the pre-reforming reactor will be the equilibrium constant corresponding to the allowable catalyst temperature at the pre-reforming reactor.

2. A methanol production method comprising:

gasifying biomass so as to produce biomass gasification gas;

removing dust in the biomass gasification gas;

desulfurizing sulfur oxide components in the biomass gasification gas that has had the dust removed therefrom so as to produce desulfurized biomass gasification gas;

reforming tar components in the desulfurized biomass gasification gas using a pre-reforming reactor, the pre-reforming reactor having a catalyst with an allowable catalyst temperature;

feeding at least one of natural gas and steam to the pre-reforming reactor during said reforming of tar components;

obtaining an equilibrium constant from partial pressures of $CH_4$, $H_2O$, CO and $H_2$ at an outlet of the pre-reforming reactor;

determining amounts of the natural gas and steam feeding to the pre-reforming reactor in said feeding at least one of natural gas and steam to the pre-reforming reactor so that the equilibrium constant that is obtained from the partial pressures of $CH_4$, $H_2O$, CO and $H_2$ at the outlet of the pre-reforming reactor will be the equilibrium constant corresponding to the allowable catalyst temperature at the pre-reforming reactor;

boosting biomass gasification gas that has been through the pre-reforming reactor to produce a boosted gas; and synthesizing methanol by using $H_2$ gas and CO gas contained in the boosted gas.

3. The methanol production method of claim 2, further comprising reforming the boosted gas so as to decrease a concentration of methane in the boosted gas.

* * * * *